United States Patent
Ladduwahetty et al.

(10) Patent No.: US 7,060,710 B2
(45) Date of Patent: Jun. 13, 2006

(54) ISOXAZOLE PYRAZOLOINDANE DERIVATIVES AS COGNITION ENHANCING GABA$_A$ α5 SUBTYPE LIGANDS

(75) Inventors: Tamara Ladduwahetty, London (GB); Angus Murray MacLeod, Bishops Stortford (GB); Kevin John Merchant, Ware (GB); Francine Sternfeld, London (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 460 days.

(21) Appl. No.: 10/301,901

(22) Filed: Nov. 22, 2002

(65) Prior Publication Data

US 2004/0006226 A1    Jan. 8, 2004

(30) Foreign Application Priority Data

Nov. 23, 2001   (GB)   .................................... 0128160

(51) Int. Cl.
| | |
|---|---|
| C07D 261/08 | (2006.01) |
| C07D 413/14 | (2006.01) |
| C07D 471/04 | (2006.01) |
| A61K 31/422 | (2006.01) |
| A61K 31/4418 | (2006.01) |

(52) U.S. Cl. ....................... 514/293; 514/338; 514/378; 546/272.1; 546/82; 548/243; 548/245; 548/247

(58) Field of Classification Search ................ 548/243, 548/245, 247; 546/272.1, 82; 514/378, 514/293, 338
See application file for complete search history.

(56) References Cited

U.S. PATENT DOCUMENTS 6,462,036 B1 * 10/2002 Doyle et al. ................. 514/218

* cited by examiner

*Primary Examiner*—Kamal A. Saeed
*Assistant Examiner*—Nyeemah Grazier
(74) *Attorney, Agent, or Firm*—John C. Todaro; Melvin Winokur

(57) ABSTRACT

The present invention provides compounds of formula I:

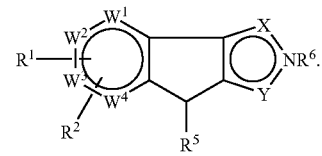

in which:

one of X and Y is a nitrogen atom substituted by a group $R^{6'}$ and the other is a carbon atom substituted by an isoxazole group substituted on its carbon atoms by groups $R^3$ and $R^4$;

one of $R^6$ and $R^{6'}$ is hydrogen;

either all of $W^1$, $W^2$, $W^3$ and $W^4$ are carbon or one of $W^1$, $W^2$, $W^3$ and $W^4$ is nitrogen and the rest are carbon;

and $R^1$ and $R^2$ are, independently, a small group, heteroaromatic ring or a 4–7 membered cyclic amine ring; processes for making them; pharmaceutical composition containing them; their use in therapy, particularly for enhancing cognition in conditions such as Alzheimer's Disease; and methods of treatment using them.

8 Claims, No Drawings

ISOXAZOLE PYRAZOLOINDANE DERIVATIVES AS COGNITION ENHANCING GABA$_A$ α5 SUBTYPE LIGANDS

CROSS REFERENCE TO RELATED APPLICATIONS

This application claims priority under 35 U.S.C. § 119 from GB Application No. 0128160.9, filed Nov. 23, 2002.

The present invention relates to a class of substituted isoxazole pyrazoloindane derivatives and to their use in therapy. More particularly, this invention is concerned with substituted 2,4-dihydroindeno[1,2-c]pyrazole and 2,8-dihydroindeno[2,1-c]pyrazole derivatives which are ligands for GABA$_A$ receptors containing the α5 subunit and are therefore useful in therapy where cognition enhancement is required. In particular it relates to compounds having an isoxazole group at the 3-position.

Receptors for the major inhibitory neurotransmitter, gamma-aminobutyric acid (GABA), are divided into two main classes: (1) GABA$_A$ receptors, which are members of the ligand gated ion channel superfamily; and (2) GABA$_B$ receptors, which maybe members of the G-protein linked receptor superfamily. Since the first cDNAs encoding individual GABA$_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the GABA$_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional GABA$_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native GABA$_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangements of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βδ, α4βδ. Subtype assemblies containing an α subunit are present in most areas of the brain and account for over 40% of GABA$_A$ receptors in the rat. Subtype assemblies containing α2 and α3 subunits respectively account for about 25% and 17% of GABA$_A$ receptors in the rat. Subtype assemblies containing an α5 subunit are primarily hippocampal and represent about 4% of receptors in the rat.

A characteristic property of some GABA$_A$ receptors is the presence of a number of modulatory sites, of which the most explored is the benzodiazepine (BZ) binding site through which anxiolytic drugs such as diazepam and temazepam exert their effect. Before the cloning of the GABA$_A$ receptor gene family, the benzodiazepine binding site was historically subdivided into two subtypes, BZ1 and BZ2, on the basis of radio ligand binding studies. The BZ1 subtype has been shown to be pharmacologically equivalent to a GABA$_A$ receptor comprising the α1 subunit in combination with β2 and γ2. This is the most abundant GABA$_A$ receptor subtype, representing almost half of all GABA$_A$ receptors in the brain.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101–108 that benzodiazepine receptor inverse agonist β-CCM enhanced spatial learning in the Morris watermaze. However, β-CCM and other conventional benzodiazepine agonists are proconvulsant, which makes it clear that they cannot be used as cognition enhancing agents in humans.

However, we have now discovered that it is possible to obtain medicaments which have cognition enhancing effects which may be employed with less risk of proconvulsant effects previously described with benzodiazepine receptor partial or full inverse agonists.

It has now been discovered that an α5 receptor partial or full inverse agonist, which is relatively free of activity at α1 and/or α2 and/or α3 receptor binding sites, can be used to provide a medicament which is useful for enhancing cognition but in which proconvulsant activity is reduced or eliminated. Inverse agonists at α5 which are not free of activity at α1 and/or α2 and/or α3 but which are functionally selective for α5 can also be used. Inverse agonists which are both selective for α5 and are relatively free of activity at α1, α2 and α3 receptor binding sites are preferred.

WO 98/50385 discloses substituted 1,2,4-triazolo[3,4-a]pyridazines which are GABA$_A$ receptor ligands selective for the α5 binding sites.

WO 98/21258 discloses substituted indeno[1,2-c]-, naphtho[1,2-c]- and benzo[6,7]cyclohepta[1,2-c]pyrazoles as tyrosine kinase inhibitors.

The present invention provides a compound of formula (I):

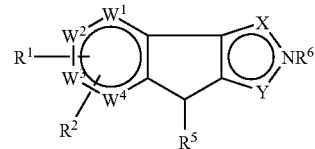

in which:

one of X and Y is a nitrogen atom substituted by a group R6' and the other is a carbon atom substituted by an isoxazole group substituted on its carbon atoms by groups $R^3$ and $R^4$;

either all of $W^1$, $W^2$, $W^3$ and $W^4$ are carbon or one of $W^1$, W2, $W^3$ and $W^4$ is nitrogen and the rest are carbon;

$R^1$ and $R^2$ are each, independently, (i) hydrogen, halogen, cyano, amino, nitro, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, hydroxy $C_{1-6}$alkyl, $C_{1-6}$alkoxy$C_{1-6}$alkyl, amino$C_{1-6}$alkyl, $C_{1-6}$alkylcarbonyl, $C_{1-6}$alkylaminocarbonyl or di($C_{1-6}$alkyl)aminocarbonyl, each of which is unsubstituted or substituted by one, two or three halogen atoms;

(ii) a 5-membered heteroaromatic ring containing 1, 2, 3 or 4 heteroatoms independently selected from O, N or S, at most one of the heteroatoms being oxygen or sulphur, or a 6-membered aromatic ring optionally containing one or two nitrogen atoms, said rings being unsubstituted or substituted by at least one substituent which is halogen, hydroxy, cyano, amino, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, $C_{1-6}$alkoxy$C_{1-6}$alkyl, hydroxy$C_{1-6}$alkyl, amino$C_{1-6}$alkyl, $C_{1-6}$alkylcarbonyl or $C_{1-6}$alkylaminocarbonyl, each of which substituents is itself, where possible, unsubstituted or substituted by one, two or three halogen atoms;

(iii) a cyclic amine ring having from 4 to 7 members, one of which is nitrogen which is the point of attachment of said ring to the rest of the molecule and optionally containing 1 additional heteroatom selected from O and N, said ring being unsubstituted or substituted by at least one substituent which is halogen, hydroxy, cyano, amino, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, $C_{1-6}$alkoxy$C_{1-6}$alkyl, amino$C_{1-6}$alkyl, $C_{1-6}$alkylcarbonyl or $C_{1-6}$alkylaminocarbonyl, each of which substituent is itself, where possible, unsubstituted or substituted by one, two or three halogen atoms;

$R^3$ and $R^4$ are independently hydrogen, halogen, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkoxy$C_{1-6}$alkyl, amino$C_{1-6}$alkyl, $C_{1-6}$alkylthio, hydroxy$C_{1-6}$alkyl, $C_{1-6}$alkylamino$C_{1-6}$alkyl, $C_{1-6}$alkylcarbonyl or $C_{1-6}$alkylaminocarbonyl, each of which is unsubstituted or substituted by one, two or three halogen atoms; or a 5-membered heteroaromatic ring containing 1, 2, 3 or 4 heteroatoms independently selected from O, N and S, at most one of the heteroatoms being oxygen or sulphur, or a 6-membered aromatic ring optionally containing 1 or 2 nitrogen atoms, the rings being unsubstituted or substituted by at least one halogen, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, hydroxy$C_{1-6}$alkyl, $C_{1-6}$alkoxy$C_{1-6}$alkyl, amino$C_{1-6}$alkyl, $C_{1-6}$alkylcarbonyl or $C_{1-6}$alkylaminocarbonyl, each of which is unsubstituted or substituted by one, two or three halogen atoms;

$R^5$ is hydrogen, halogen, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, $C_{1-6}$alkoxy$C_{1-6}$alkyl, amino$C_{1-6}$alkyl, $C_{1-6}$alkylcarbonyl or $C_{1-6}$alkylaminocarbonyl; and one of $R^6$ and $R^{6'}$ is hydrogen;

or a pharmaceutically acceptable salt thereof.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{2-6}$alkenyl", "$C_{2-6}$alkynyl", "hydroxy$C_{1-6}$alkyl", "$C_{1-6}$alkylthio", "$C_{1-6}$alkylaminocarbonyl", "$C_{1-6}$alkylcarbonyl", and "amino$C_{1-6}$alkyl" are to be construed in an analogous manner.

Unless otherwise specified, 5- and 6-membered heterocyclic rings shall include pyridinyl, pyridazinyl, pyrmidinyl, pyrazinyl, pyrrolyl, furyl, thienyl, pyrazolyl, oxazolyl, isoxazolyl, thiazolyl, isothiazolyl, imidazolyl, oxadiazolyl, thiadiazolyl and triazolyl groups. Suitable 6-membered heterocyclic rings containing 3 nitrogen atoms include 1,2,4-triazine and 1,3,5-triazine. When a heterocyclic ring comprises a hydroxy group as a susbstituent, and keto-enol tautomerism is possible, both tautomers are included within the scope of the invention.

The expression "5- or 6-membered aromatic ring" will, unless otherwise specified, include phenyl.

The term "halogen" as used herein includes fluorine, chlorine, bromine and iodine, of which fluorine and chlorine are generally preferred.

As used herein the term "$C_{1-6}$alkoxy" includes methoxy and ethoxy groups, and straight-chained and branched propoxy, butoxy, pentoxy and hexoxy groups. Derived expressions such as "$C_{2-6}$alkenyloxy", "$C_{2-6}$alkynyloxy" and "$C_{1-6}$alkoxy$C_{1-6}$alkyl", should be construed in an analogous manner.

The term "cyclic amine" as used herein shall refer to ring containing from 4 to 7 members. Such groups may contain one or two further heteroatoms, these being selected from oxygen and nitrogen. Typical such cyclic amine groups will include azetidinyl, pyrrolidinyl, piperidinyl, piperazinyl, pyrazolidinyl, imidazolidinyl and morpholinyl.

Generally $W^1$ is nitrogen or carbon and $W^2$, $W^3$ and $W^4$ are carbon. Preferably all of $W^1$, $W^2$, $W^3$ and $W^4$ are carbon.

In a preferred subset of the compounds of formula (I), $R^1$ is typically hydrogen, halogen, cyano, $C_{1-4}$alkyl, $C_{1-4}$alkoxy, $C_{1-4}$alkylaminocarbonyl, di($C_{1-4}$alkyl)aminocarbonyl, aminocarbonyl, a 5- or 6-membered heterocyclic ring containing 1 or 2 nitrogen heteroatoms or 1 sulphur heteroatom and optionally substituted by a $C_{1-6}$alkyl group. In particular $R^1$ can be hydrogen, methoxy, cyano, aminocarbonyl, 2-methylpyrazol-3-yl, methylaminocarbonyl, dimethylaminocarbonyl, ethylaminocarbonyl, 1-methylimidazol-2-yl, pyrid-3-yl or pyrid-4-yl.

$R^2$ is preferably hydrogen or $C_{1-4}$ alkoxy, particularly hydrogen or methoxy. $R^2$ may be hydrogen.

Generally the isoxazole group on X or Y is an isoxazol-4-yl group. In this case the group $R^3$ is on the 5-position and the group $R^4$ is on the 3-position.

Then, preferably, $R^3$ is independently hydrogen, halogen, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkoxy$C_{1-6}$alkyl, amino$C_{1-6}$alkyl, $C_{1-6}$alkylthio, hydroxy$C_{1-6}$alkyl, $C_{1-6}$alkylamino$C_{1-6}$alkyl, $C_{1-6}$alkylcarbonyl or $C_{1-6}$alkylaminocarbonyl, each of which is unsubstituted or substituted by one, two or three halogen atoms.

In particular $R^3$ is $C_{1-6}$alkyl, such as $C_{1-4}$alkyl, such as methyl.

Then, preferably, $R^4$ is a 5-membered heteroaromatic ring containing 1, 2, 3 or 4 heteroatoms independently selected from O, N and S, at most one of the heteroatoms being oxygen or sulphur, or a 6-membered aromatic ring optionally containing 1 or 2 nitrogen atoms, the rings being unsubstituted or substituted by at least one halogen, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, hydroxy$C_{1-6}$alkyl, $C_{1-6}$alkoxy$C_{1-6}$alkyl, amino$C_{1-6}$alkyl, $C_{1-6}$alkylcarbonyl or $C_{1-6}$alkylaminocarbonyl, each of which is unsubstituted or substituted by one, two or three halogen atoms.

In the compounds of formula (I), we generally prefer that $R^4$ represents a 5- or 6-membered aromatic ring optionally containing 1 nitrogen heteroatom, the ring being unsubstituted or substituted by at least one halogen, hydroxy, $C_{1-4}$alkyl, $C_{2-4}$alkenyl, $C_{1-4}$alkoxy, hydroxy$C_{1-4}$alkyl, $C_{1-4}$alkoxy$C_{1-4}$alkyl, amino$C_{1-4}$alkyl, $C_{1-4}$alkylcarbonyl or $C_{1-4}$alkylaminocarbonyl, each of which is unsubstituted or substituted by one, two or three halogen atoms. It is more preferred that $R^4$ represents phenyl optionally substituted by a halogen or pyridinyl group. $R^4$ may especially be phenyl, 4-fluorophenyl, 2-fluorophenyl or pyrid-4-yl.

Typically $R^5$ is hydrogen, halogen, hydroxy, $C_{1-4}$alkyl, $C_{1-4}$alkoxy, $C_{1-4}$alkoxyC$_{1-4}$alkyl or aminoC$_{1-4}$alkyl. We generally prefer that $R^5$ represents hydrogen, $C_{1-4}$alkyl or a phenyl group, most preferably hydrogen, methyl or phenyl, especially hydrogen.

In a preferred embodiment of the present invention we provide a compound of formula (I), as shown above, in which:

$R^1$ and $R^2$ each, independently, represents hydrogen, fluoro, chloro, bromo, cyano, $C_{1-6}$alkyl, $C_{1-6}$alkoxy, aminocarbonyl, $C_{1-6}$alkylaminocarbonyl, di($C_{1-6}$)alkylaminocarbonyl, N,N-diethylaminocarbonyl, pyridyl or methylimidazolyl;

$R^3$ represents a methyl group;

$R^4$ represents phenyl, fluorophenyl or pyridyl;

$R^5$ represents hydrogen; and one of $R^6$ and $R^{6'}$ represents hydrogen;

or a pharmaceutically acceptable salt thereof.

Preferred definitions above apply mutatis mutandis, where posible, to this subset of compounds.

Representative of the present invention are the following compounds:

3-(5-methyl-3-phenylisoxazol-4-yl)-2,4-dihydroindeno[1,2-c]pyrazole;

3-(5-methyl-3-phenylisoxazol-4-yl)-2,8-dihydroindeno[2,1-c]pyrazole;

6-methoxy-3-(5-methyl-3-phenylisoxazol-4-yl)-2,4-dihydroindeno[1,2-c]pyrazole;

7-methoxy-3-(5-methyl-3-phenylisoxazol-4-yl)-2,4-dihydroindeno[1,2-c]pyrazole;

5-methoxy-3-(5-methyl-3-phenylisoxazol-4-yl)-2,4-dihydroindeno[1,2-c]pyrazole;

6,7-dimethoxy-3-(5-methyl-3-phenylisoxazol-4-yl)-2,4-dihydroindeno[1,2-c]pyrazole;

3-(5-methyl-3-phenylisoxazol-4-yl)-2,4-dihydroindeno[1,2-c]pyrazole-6-carbonitrile;

3-(5-methyl-3-phenylisoxazol-4-yl)-2,4-dihydroindeno[1,2-c]pyrazole-6-carboxylic acid amide;

3-(5-methyl-3-phenylisoxazol-4-yl)-5-(2-methyl-2H-pyrazol-3-yl)-2,4-dihydroindeno[1,2-c]pyrazole;

3-(5-methyl-3-phenylisoxazol-4-yl)-2,4-dihydroindeno[1,2-c]pyrazole-6-carboxylic acid methylamide;

3-(5-methyl-3-phenylisoxazol-4-yl)-2,4-dihydroindeno[1,2-c]pyrazole-6-carboxylic acid dimethylamide;

3-(5-methyl-3-phenylisoxazol-4-yl)-2,4-dihydroindeno[1,2-c]pyrazole-6-carboxylic acid ethylamide;

6-(1-methyl-1H-imidazol-2-yl)-3-(5-methyl-3-phenylisoxazol-4-yl)-2,4-dihydroindeno[1,2-c]pyrazole;

3-(5-methyl-3-phenylisoxazol-4-yl)-6-pyridin-3-yl-2,4-dihydroindeno[1,2c]pyrazole;

3-(5-methyl-3-phenylisoxazol-4-yl)-6-pyridin-4-yl-2,4-dihydroindeno[1,2c]pyrazole;

3-[3-(4-fluorophenyl)-5-methylisoxazol-4-yl]-2,4-dihydroindeno[1,2-c]pyrazole;

3-[3-(2-fluorophenyl)-5-methylisoxazol-4-yl]-2,4-dihydroindeno[1,2-c]pyrazole;

3-[3-(4-fluorophenyl)-5-methylisoxazol-4-yl]-6,7-dimethoxy-2,4-dihydroindeno[1,2-c]pyrazole;

3-(5-methyl-3-(4-pyridyl)isoxazol-4-yl)-2,4-dihydroindeno[1,2-c]pyrazole;

and 1-(5-methyl-3-phenylisoxazol-4-yl)-2,8-dihydro-2,3,4-triazacyclopenta[a]indene;

or a pharmaceutically acceptable salt thereof.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the present invention.

For use in medicine, the compounds of formula (I) may be in the form of pharmaceutically acceptable salts. Hence in a favoured aspect this invention provides the compounds of formula (I) in the form of pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts and salts formed with suitable organic ligands, e.g. quaternary ammonium salts.

The compounds of the present invention have a good binding affinity (Ki) for the α5 subunit of the GABA$_A$ receptor. In a preferred embodiment the compounds of the present invention are binding selective for the α5 subunit relative to the α1, α2 and α3 subunits. In another preferred embodiment the compounds are functionally selective for the α5 subunit as partial or full inverse agonists whilst substantially being antagonists at the α1, α2 and α3 subunits. Particularly preferred are compounds which are both binding and functionally selective.

The invention also provides pharmaceutical compositions comprising one or more compounds of this invention and a pharmaceutically acceptable carrier. Preferably these compositions are in unit dosage form, such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or unsufflation. For preparing solid compositions such as tablets, the principal active ingredient is mixed with a pharmaceutical carrier, e.g. conventional tableting ingredients, such as corn starch, lactose, sucrose, sorbitol, talc, stearic acid, magnesium stearate, dicalcium phosphate or gums or surfactants, such as sorbitan monooleate, polyethylene glycol and other pharmaceutical diluents, e.g. water, to form a solid preformulation composition containing a homogeneous mixture of a compound of the present invention, or a pharmaceutically acceptable salt thereof. When referring to these preformulations as homogeneous, it is meant that the active ingredient is dispersed evenly throughout the composition so that the composition may be readily subdivided into equally effective unit dosage forms, such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention for use in a method of treatment in the human body. Preferably the treatment is for a condition associated with $GABA_A$ receptors comprising the α5 subunit and/or for enhancement of cognition. Preferably the condition is a neurological deficit with an associated cognitive disorder such as a dementing illness such as Alzheimer's disease. Other conditions to be treated include cognition deficits due to traumatic injury, stroke, Parkinson's disease, Downs syndrome, age related memory deficits, attention deficit disorder and the like.

The present invention further provides the use of a compound of the present invention in the manufacture of a medicament for the enhancement of cognition, preferably in a human being suffering from a dementing illness such as Alzheimer's disease.

Also disclosed is a method of treatment of a subject suffering from a cognition deficit, such as that resulting from a dementing illness such as Alzheimer's disease, which comprises administering to that subject an effective amount of a compound according to the present invention.

The liquid forms in which the novel compositions of the present invention may be incorporated for administration orally or by injection include aqueous solutions, suitably flavoured syrups, aqueous or oil suspensions and flavoured emulsions with edible oils such as cottonseed oil, sesame oil, coconut oil or peanut oil as well as elixirs and similar pharmaceutical vehicles. Suitable dispersing or suspending agents for aqueous suspensions include synthetic and natural gums, such as tragacanth, acacia, alginate, dextran, sodium carboxymethylcellulose, methylcellulose, polyvinyl-pyrrolidone or gelatin.

For the enhancement of cognition, a suitable dosage level is about 0.01 to 250 mg/kg per day, preferably about 0.01 to 100 mg/kg per day and especially about 0.01 to 5 mg/kg of body weight per day. The compounds may be administered on a regimen of 1 to 4 times per day. In some cases, however, dosage outside these limits may be used.

The present invention also provides a process for the preparation of the compounds of formula (I), as defined above, which comprises:

(i) reacting a compound of formula II or II':

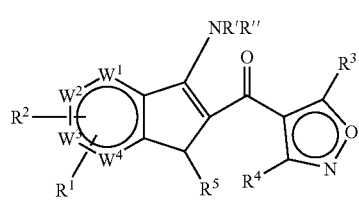

(II)

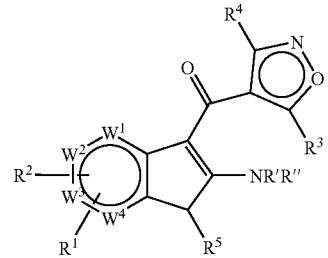

(II')

in which $R^1$, $R^2$, $R^3$, $R^4$, $R^5$, $W^1$, $W^2$, $W^3$ and $W^4$ are as defined above, and R' and R" are $C_{1-6}$alkyl groups which, together with the nitrogen atom to which they are attached, optionally form a cyclic amine, with hydrazine, preferably in the form of its hydrochloride, suitably in the presence of an organic solvent, such as aqueous ethanol, at about 80° C. for about 36 h.

The compound of formula II is prepared by reacting a compound of formula III with a compound of formula IV:

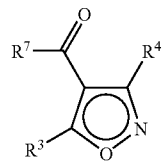

(III)

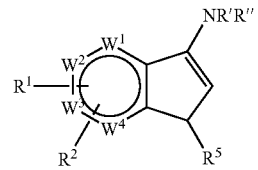

(IV)

wherein R', R", $R^1$, $R^2$, $R^3$, $R^4$, $R^5$, $W^1$, $W^2$, $W^3$ and $W^4$ are as defined above and $R^7$ is chlorine, generally in a solvent such as dichloromethane in the presence of a base such as triethylamine at about room temperature for about 2 h.

The compound of formula II" is made similarly from a compound of formula III and a compound of formula V:

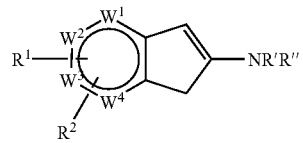

(V)

wherein R', R", $R^1$, $R^2$, $W^1$, $W^2$, $W^3$, $W^4$ and P are as defined above.

The compounds of formulae IV and V can be prepared by reacting a compound of formula VI or VII with a compound of formula HNR'R":

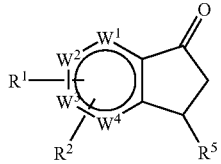

(VI)

-continued (VII)

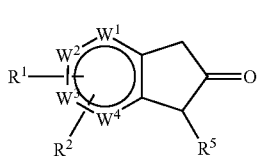

where $R^1$, $R^2$, $R^5$, $W^1$, $W^2$, $W^3$ and $W^4$ are as defined above.

The compounds of formulae VI and VII are commercially available or can be made from commercially available compounds by known methods.

Alternatively compounds of formula I can be prepared by reacting a compound of formula VIII or VIII' with p-toluenesulfonyl hydrazide (VIII)

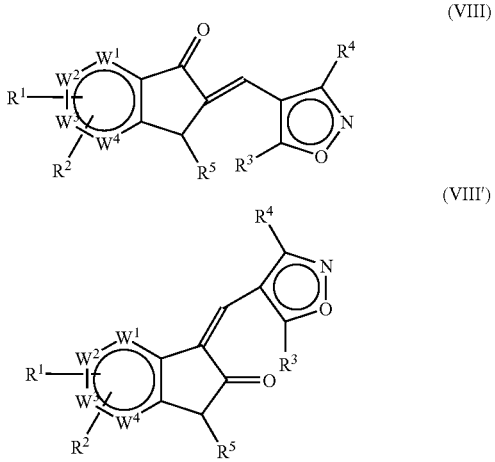

(VIII')

wherein $R^1$, $R^2$, $R^3$, $R^4$, $R^5$, $W^1$, $W^2$, $W^3$ and $W^4$ are as defined above, generally in a solvent such as THF at reflux for about 48 h.

The compounds of formulae VIII and VIII' can be prepared by reacting a compound of formula VI or VII respectively with a compound of formula III in which $R^7$ is hydrogen, generally in a solvent such as ethanol in the presence of a base such as NaOH at reflux for about 17 h.

In a further alternative a compound of formula I may be prepared by successively reacting a compound of formula VI or VII with a compound of formula III in which $R^7$ is hydroxy. In this reaction the compound of formula III is preactivated for example with N,N-carbonyldiimidazole and 4-dimethylaminopyridine and treated with the anion of the compound of formula VI or VII at low temperature.

Compounds of formula III in which $R^7$ is hydrogen can be made by reacting a compound of formula III in which $R^7$ is $(CH_3O)(CH_3)NCO$ with a reducing agent such as lithium aluminium hydride generally in a solvent such as THF at about 0° C. for about 20 min.

The compound of formula III in which $R^7$ is $(CH_3O)(CH_3)NCO$ can be prepared by reacting a compound of formula III in which $R^7$ is $CH_3OCO$ with N,O-dimethylhydroxylamine, generally as its hydrochloride in a solvent such as THF at about –20° C. together with isopropylmagnesium chloride (to activate the amine) for about 30 min.

The compound of formula III in which $R^7$ is $CH_3O$ can be produced by reacting a compound of formula IX with a compound of formula X:

(IX)

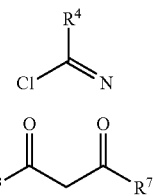

(X)

wherein $R^3$ and $R^4$ are as defined above, generally under basic conditions, such as sodium methoxide in methanol, for about 16 h at room temperature.

Other compounds of formula III are commercially available.

In an alternative process a compound of formula I is produced by reacting a compound of formula XI:

(XI)

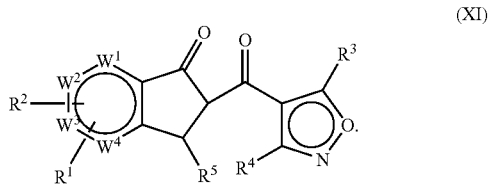

in which $W^1$, $W^2$, $W^3$, $W^4$, $R^1$, $R^2$, $R^3$, $R^4$ and $R^5$ are as defined above, with hydrazine hydrochloride, generally in the presence of sodium acetate trihydride in a 1:1 ethanol/water mixture at reflux under nitrogen for about 21 hours.

The compound of formula XI is prepared by reacting a compound of formula XII:

(XII)

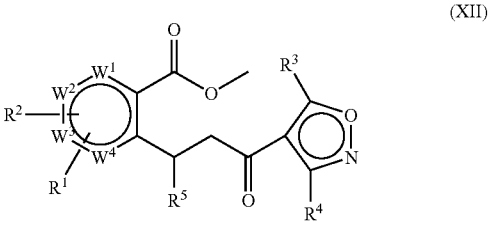

in which $W^1$, $W^2$, $W^3$, $W^4$, $R^1$, $R^2$, $R^3$, $R^4$ and $R^5$ are as defined above, with a strong base such as sodium hydride generally in a solvent such as tetrahydrofuran at about 0° C. under $N_2$ for about 70 minutes and at room temperature for about 15 minutes.

The compound of formula XII is prepared by reacting a compound of formula XII:

(XIII)

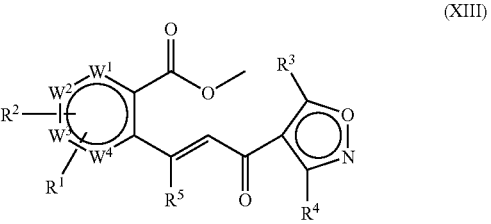

in which $W^1$, $W^2$, $W^3$, $W^4$, $R^1$, $R^2$, $R^3$, $R^4$ and $R^5$ are as defined above, with a reducing agent such as hydrogen in the presence of a catalyst such as 10% Pd on C usually in a solvent such as ethanol and with protection against reduction of the isoxazole group with a compound such as perchloric acid.

The compound of formula XIII can be made by reacting a compound of formula XIV with a compound of formula XV:

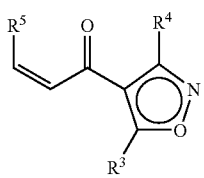
(XIV)

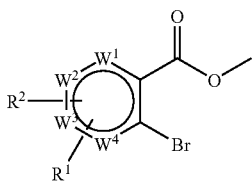
(XV)

in which $W^1$, $W^2$, $W^3$, $W^4$, $R^1$, $R^2$, $R^3$, $R^4$ and $R^5$ are as defined above utilising a catalyst such as palladium acetate generally in the presence of tri(o-tolyl)phosphine, a base such as triethylamine and copper (I) iodide at reflux for several hours, in a solvent such as acetonitrile.

The compound of formula XIV can be made by reacting a compound of formula XVI with a compound of formula XVII:

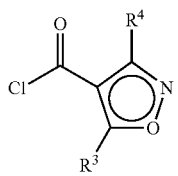
(XVI)

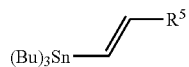
(XVII)

in which $R^3$, $R^4$ and $R^5$ are as defined above, in the presence of a catalyst such as trans-benzyl(chloro)bis(triphenylphosphine)palladium(II) generally in a solvent such as chloroform at about room temperature for about three hours.

The compound of formula XV can be made by reacting a compound of formula XVIII:

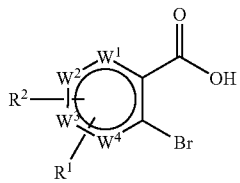
(XVIII)

in which $W^1$, $W^2$, $W^3$, $W^4$, $R^1$ and $R^2$ are as defined above, sequentially with a strong base such as NaH, generally in a solvent such as DMF, at about 0° C. under nitrogen for about 50 min and then with a methylating agent such as MeI generally with warming to about room temperature over about two days.

Compounds of formula IX, X, XVI, XVII and XVIII are commercially available or can be made by known methods from commercially available compounds.

It will be understood that any compound of formula (I) initially obtained from the above process may, where appropriate, subsequently be converted into a further compound of formula (I) by techniques known from the art as illustrated by the Examples.

It will also be appreciated that where more than one isomer can be obtained from a reaction then the resulting mixture of isomers can be separated by conventional means.

Where the above described process for the preparation of compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-d-tartaric acid, followed by fractional crystallisation and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the present invention.

EXAMPLE 1

3-(5-Methyl-3-phenylisoxazol-4-yl)-2,4-dihydroindeno[1,2-c]pyrazole a) 1-(3H-Inden-1-yl)pyrrolidine To a 100 ml reaction tube equipped with a stirrer bar, Suba.Seal™ stopper, and a nitrogen balloon, was added pyrrolidine (1.3 ml) and pentane (8 ml). Titanium tetrachloride (0.2 ml) was added slowly to each tube. 1-Indanone (0.2 g, 1.33 mmol) was added as a solid and the reaction stirred vigorously for 2 h. The reaction mixture was filtered through Celite and the solvent removed in vacuo to give the title compound as a dark solid. m/z (ES⁺) 186 (M+H)⁺.

b) (5-Methyl-3-phenylisoxazol-4-yl)(3-pyrrolidin-1-yl-1H-inden-2-yl)-methanone

The solid obtained from step a) was dissolved in dichloromethane (20 ml) and cooled to 0° C. Triethylamine (1 ml, 7.5 mmol) was added followed by 3-phenyl-5-methyl-4-isoxazolecarbonyl chloride (0.9 ml (1.8 mmol) of a 1.96M solution in dichloromethane. The reaction was warmed to 25° C. and stirred for 2 h. Water (10 ml) was added and the reaction mixture extracted into dichloromethane. The organic layer was dried (MgSO$_4$) and evaporated to obtain the title compound as a brown oil m/z (ES$^+$) 371(M+H)$^+$.

c) 3-(5-Methyl-3-phenylisoxazol-4-yl)-2,4-dihydroindeno[1,2-c]pyrazole

The compound from step b) was dissolved in EtOH (30 ml) and treated with hydrazine monohydrochloride (1.0 g, 13.3 mmol). The reaction vessel was fitted with an air-cooled condenser and heated to 80° C. for 36 h. The reaction mixture was cooled, water (10 ml) added, and the ethanol removed in vacuo. The residue was partitioned between EtOAc and water and the organic layer washed with water (2×). The organic layer was dried over MgSO$_4$, evaporated, and the residue purified on alumina (Grade III), eluting with 0.5% EtOH/CH$_2$Cl$_2$ to obtain the title compound as a white solid (20.5 mg). $^1$H NMR (400 MHz, CDCl$_3$) δ 7.72 (brs, 1H), 7.52 (d, J=7.6 Hz, 2H), 7.43–7.34 (m, 5H), 7.28 (t, J=9.6 Hz, 2H), 3.3 (brs, 2H), 2.56 (s, 3H), m/z (ES$^+$) 314 (M+H)$^+$.

EXAMPLE 2

3-(5-Methyl-3-phenylisoxazol-4-yl)-2,8-dihydroindeno[2,1-c]pyrazole a) 1-(1H-Inden-2-yl)pyrrolidine To a 100 ml reaction tube equipped with a stirrer bar, Suba.Seal™ stopper, and a nitrogen balloon, was added pyrrolidine (1.3 ml) and pentane (8 ml). Titanium tetrachloride (0.2 ml) was added slowly to each tube. 2-Indanone (0.2 g, 1.33 mmol) was added as a solid and the reaction stirred vigorously for 2 h. The reaction mixture was filtered through Celite and the solvent removed in vacuo to give the title compound as a dark solid. m/z (ES$^+$) 186 (M+H)$^+$.

b) (5-Methyl-3-phenylisoxazol-4-yl)(2-pyrrolidin-1-1-3H-inden-1-yl)-methanone

The solid obtained from step a) was dissolved in dichloromethane (20 ml) and cooled to 0° C. Triethylamine (1 ml, 7.5 mmol) was added followed by 3-phenyl-5-methyl-4-isoxazolecarbonyl chloride (0.9 ml (1.8 mmol) of a 1.96M solution in dichloromethane). The reaction was warmed to 25° C. and stirred for 2 h. Water (10 ml) was added and the reaction mixture extracted into dichloromethane. The organic layer was dried (MgSO$_4$) and evaporated to obtain the title compound as a brown oil m/z (ES$^+$) 371 (M+H)$^+$.

c) 3-(5-Methyl-3-phenylisoxazol-4-yl)-2,8-dihydroindeno[2,1-c]pyrazole

The compound from step b) was dissolved in EtOH (30 ml) and treated with hydrazine monohydrochloride (1.0 g, 13.3 mmol). The reaction vessel was fitted with an air-cooled condenser and heated to 80° C. for 36 h. The reaction mixture was cooled, water (10 ml) added, and the ethanol removed in vacuo. The residue was partitioned between EtOAc and water and the organic layer washed with water (2×). The organic layer was dried over MgSO$_4$, evaporated, and the residue purified on alumina (Grade III), eluting with 0.5% EtOH/CH$_2$Cl$_2$ to obtain the title compound as a white solid (18.3 mg). $^1$H NMR (400 MHz, CDCl$_3$) δ 7.54 (d, J=7.2 Hz, 2H), 7.47 (d, J=6.0 Hz, 1H), 7.39–7.30 (m, 3H), 7.21–7.17 (m, 2H), 7.09 (d, J=7.2 Hz, 1H), 3.8 (s, 2H), 2.5 (s, 3H), m/z (ES$^+$) 314 (M+H)$^+$.

EXAMPLE 3

6-Methoxy-3-(5-methyl-3-phenylisoxazol-4-yl)-2,4-dihydroindeno[1,2-c]pyrazole a) 5-Methoxy-2-(5-methyl-3-phenylisoxazol-4-ylmethylene)indan-1-one 5-Methoxy-1-indanone (1 g, 6.2 mmol) and 3-phenyl-5-methyl-4-isoxazolecarbaldehyde (1.14 g, 6.2 mmol) were dissolved in EtOH (30 ml) and NaOH(4 drops of a 4M solution in water) was added. The reaction mixture was heated to reflux for 17 h. The reaction mixture was cooled and filtered to obtain the title compound as a yellow solid (1.0 g, 49%).

b) 6-Methoxy-3-(5-methyl-3-phenylisoxazol-4-yl)-2,4-dihydroindeno[1,2-c]pyrazole A mixture of compound from step a) (1.0 g, 3.0 mmol), p-toluenesulfonyl hydrazide (1.12 g, 6.0 mmol), and HCl (conc., 1 drop) in THF (30 ml) was heated to reflux for 48 h. The solvent was removed and the residue dissolved in EtOH and treated with K$_2$CO$_3$ (1.24 g, 9.0 mmol) and the reaction heated to reflux for 0.5 h. The reaction mixture was cooled and ethanol removed in vacuo. The residue was partitioned between EtOAc and water and the organic layer collected and washed in brine, dried over MgSO$_4$ and evaporated. The residue was chromatographed on silica, eluting with 20% EtOAc/hexane to obtain the title compound as a white solid (0.055 g). $^1$H NMR (360 MHz, CDCl$_3$) δ 7.60 (d, J=8.3 Hz, 1H), 7.53–7.50 (m, 2H), 7.41–7.33 (m, 3H), 6.97 (s, 1H), 6.90 (dd, J=8.3 Hz, 2.3 Hz, 1H), 3.84 (s, 3H), 3.25 (s, 2H), 2.6 (s, 3H). m/z (ES$^+$) 339 (M+H)$^+$.

EXAMPLE 4

7-Methoxy-3-(5-methyl-3-phenylisoxazol-4-yl)-2,4-dihydroindeno[1,2-c]pyrazole

Prepared in the same way as Example 1 using 6-methoxy-1-indanone to obtain the title compound as a white solid (27 mg, 5%). 1H NMR (360 MHz, CDCl$_3$) δ 7.53–7.51 (m, 2H), 7.43–7.26 (m, 5H), 6.85 (dd, J=8.3, 2.4 Hz, 1H), 3.87 (s, 3H), 3.27 (s, 2H), 2.57 (s, 3H), m/z (ES$^+$) 344 (M+H)$^+$.

EXAMPLE 5

5-Methoxy-3-(5-methyl-3-phenylisoxazol-4-yl)-2,4-dihydroindeno[1,2-c]pyrazole

Prepared in the same way as Example 1 using 4-methoxy-1-indanone to obtain the title compound as a white solid (18 mg, 3%). $^1$H NMR (360 MHz, CDCl$_3$) δ 7.52 (d, J=7.4 Hz, 2H), 7.43–7.33 (m, 5H), 6.85 (d, J=7.2 Hz, 1H), 3.89 (s, 3H), 3.33 (s, 2H), 2.56 (s, 3H), m/z (ES$^+$) 344 (M+H)$^+$.

EXAMPLE 6

6,7-Dimethoxy-3-(5-methyl-3-phenylisoxazol-4-yl)-2,4-dihydroindeno[1,2-c]pyrazole 5,6-Dimethoxy-1-indanone (1.92 g, 10 mmol) in tetrahydrofuran (10 ml) was added dropwise to a solution of lithium diisopropylamide (10 mmol) in tetrahydrofuran (10 ml) at −78° C. and stirred for 0.5 h. 5-Methyl-3-phenylisoxazole-4-carboxylic acid (1.02 g, 5 mmol) was stirred with N,N'-carbonyldiimidazole (810 mg, 5 mmol) in tetrahydrofuran (5 ml) for 1 h and then added to the dimethoxyindanone solution with 4-dimethylaminopyridine (610 mg, 5 mmol). This was stirred at −78° C. for 1.5 h and warmed to RT over 2 h then diluted with EtOAc, washed with citric acid solution, brine, dried (MgSO$_4$) and evaporated. The resulting yellow oil was dissolved in ethanol (5 ml), saturated copper acetate solution (10 ml) was added and the precipitate formed was filtered off and washed with H$_2$O, methanol, diethyl ether, dried (MgSO$_4$) and evaporated. The residue was dissolved in ethanol, hydrazine hydrochloride (500 mg) and sodium acetate (1 g) and H$_2$O were added and heated to reflux for 24 h. The solvent was evaporated, the residue dissolved in EtOAc, washed with brine, dried (MgSO$_4$) and evaporated. Purified by prep HPLC to give the title compound (7 mg). 1H NMR (360 MHz, CDCl$_3$) δ 7.52 (d, J=6.8 Hz, 2H), 7.43–7.33 (m, 5H), 3.94 (s, 3H), 3.91 (s, 3H), 3.28 (s, 2H), 2.57 (s, 3H), m/z (ES$^+$) 374 (M+H)$^+$.

EXAMPLE 7

3-(5-Methyl-3-phenylisoxazol-4-yl)-2,4-dihydroindeno[1,2-c]pyrazole-6-carbonitrile A suspension of 6-bromo-3-(5-methyl-3-phenylisoxazol-4-yl)-1,4-dihydroindeno[1,2-c]pyrazole (500 mg, 1.3 mmol) (prepared from 5-bromoindane in the same manner as Example 1) and zinc cyanide (912 mg, 7.8 mmol) in DMF (5 ml) was degassed with N$_2$ for 0.5 hr, tetrakis(triphenylphosphine)palladium(0) (100 mg) was added and heated to 80° C. for 3 days. The reaction mixture was cooled, poured into 10% ammonium hydroxide solution and extracted into EtOAc. The organic layer was washed with H$_2$O(×3) then dried (MgSO$_4$), evaporated and the residue chromatographed on silica, eluting with dichloromethane and recrystallised from hot dichloromethane to give the title compound as a white solid (55 mg, 13%). $^1$H NMR (400 MHz, CDCl$_3$) δ 7.84 (d, J=8.4 Hz, 1H), 7.68 (d, J=7.6 Hz, 2H), 7.51–7.37 (m, 5H), 3.35 (s, 2H), 2.59 (s, 3H), m/z (ES$^+$) 339 (M+H)$^+$.

EXAMPLE 8

3-(5-Methyl-3-phenylisoxazol-4-yl)-2,4-dihydroindeno[1,2-c]pyrazole-6-carboxylic acid amide A solution of 6-bromo-3-(5-methyl-3-phenylisoxazol-4-yl)-1,4-dihydroindeno[1,2-c]pyrazole (250 mg, 0.6 mmol), hexamethyldisilazane (0.9 ml, 4.2 mmol), diisopropylethylamine (0.2 ml, 1.2 mmol) and 1,3-bis(diphenylphosphino)propane (25 mg, 0.06 mmol) in 1,3-dimethyl-3,4,5,6-tetrahydro-2(1H)-pyrimidinone (5 ml) was degassed with nitrogen for 0.5 h, Pd(OAc)$_2$ (13 mg, 0.06 mmol) was added and carbon monoxide was bubbled through the reaction whilst heating to 100° C. After 2 h the stream of carbon monoxide was replaced with a balloon of carbon monoxide and the reaction was heated at 100° C. for 16 h. The reaction was cooled, partitioned between H$_2$O and EtOAc and the organic layer washed with H$_2$O (×10), dried (MgSO$_4$) and evaporated. The residue was chromatographed on silica, eluting with 3% methanol/dichloromethane to give a yellow oil which was crystallised from CDCl$_3$ to give the title compound as a white solid (40 mg, 19%). $^1$H NMR (360 MHz, CDCl$_3$) δ 7.92 (s, 1H), 7.81 (s, 1H), 7.51 (d, J=6.8 Hz, 2H), 7.47–7.37 (m, 3H), 3.33 (s, 2H), 2.60 (s, 3H), m/z (ES$^+$) 357 (M+H)$^+$.

EXAMPLE 9

3-(5-Methyl-3-phenylisoxazol-4-yl)-5-(2-methyl-2H-pyrazol-3-yl)-2,4-dihydroindeno[1,2-c]pyrazole a) 1-(5-polystyrenemethoxymethyltetrahydropyran-2-yl)-5-bromo-3-(5-methyl-3-phenylisoxazol-4-yl)-1,4-dihydroindeno-[1,2-c]pyrazole 5-Bromo-3-(5-methyl-3-phenylisoxazol-4-yl)-2,4-dihydroindeno[1,2-c]pyrazole (prepared from 4-bromoindan-1-one in a similar manner to example 3) (0.782 g) and 3,4-dihydro-2H-pyran-5-ylmethoxymethyl polystyrene (11.2 g) and pyridine toluenesulfonate (0.17 g) were heated in 1,2-dichloroethane for 16 hours. The resin was washed sequentially with DMF, THF, dichloromethane (×5) and then sequentially with methanol, dichloromethane and ether (×3) and dried to yield title compound.

b) 3-(5-Methyl-3-phenylisoxazol-4-yl)-5-(2-methyl-2H-pyrazol-3-yl)-2,4-dihydroindeno[1,2-c]pyrazole To compound from step a) (1 g) and 1-methyl-5-tributylstannanyl-1H-pyrazole (370 mg, 1 mmol) in DMF (5 ml) was added a solution of bis(triphenylphosphine)palladium (II) chloride (10 mg) in DMF and heated to 100° C. for 16 h. The reaction was cooled and filtered and the resin washed with DMF (×5), THF (×5), dichloromethane (×5), alternating methanol/dichloromethane (×3) and diethyl ether. The resin was then stirred with dichloromethane and 95% trifluoroacetic acid for 16 h, filtered and washed with alternating methanol/dichloromethane (×2) and evaporated. The residue was dissolved in EtOAc and washed with potassium carbonate solution, dried (MgSO$_4$) and evaporated and chromatographed on silica eluting with 40% EtOAc/dichloromethane to give the title compound (10 mg, 14%). $^1$H NMR (360 MHz, CDCl$_3$) δ 7.82 (d, J=7.5 Hz, 1H), 7.55 (d, J=1.8 Hz, 1H), 7.50–7.33 (m, 6H), 7.23 (d, J=7.7 Hz, 1H), 6.23 (d, J=1.9 Hz, 1H), 3.73 (s, 3H), 3.12 (s, 2H), 2.55 (s, 3H), m/z (ES$^+$) 394 (M+H)$^+$.

EXAMPLE 10

3-(5-Methyl-3-phenylisoxazol-4-yl)-2,4-dihydroindeno[1,2-c]pyrazole-6-carboxylic acid methylamide a) 3-(5-Methyl-3-phenylisoxazol-4-yl)-2,4-dihydroindeno[1,2-c]pyrazole-6-carboxylic acid To a solution of 6-bromo-3-(5-methyl-3-phenylisoxazol-4-yl)-1,4-dihydroindeno[1,2-c]pyrazole (1 g, 2.6 mmol), triethylamine (0.7 ml, 5.2 mmol) and 1,1'-bis(diphenylphosphino)ferrocene (178 mg, 0.32 mmol) in methanol (5 ml) and N,N-dimethylformamide (10 ml) in a sealed tube filled with carbon monoxide was added Pd(OAc)$_2$ (36 mg, 0.16 mmol) and the mixture heated to 100° C. for 16 h. The solvent was evaporated, the residue dissolved in ethanol and treated with sodium hydroxide (13 mmol) at 0° C. and allowed to warm to RT. The solvent was evaporated, the residue partitioned between H$_2$O and EtOAc and the product extracted into the aqueous layer which was then washed with diethyl ether (×3). The aqueous was cooled, acidified and extracted into EtOAc, the organic layer was then extracted with ammonium hydroxide solution (×2) and the aqueous cooled to 0° C. and acidified with conc HCl, left to stand at 0° C until the title compound appeared as a precipitate. $^1$H NMR (360 MHz, CDCl$_3$) δ 8.08 (t, J=7.8 Hz, 1H), 7.77 (d, J=7.8 Hz, 1H), 7.51 (d, J=7.6 Hz, 1H), 7.45–7.35 (m, 3H), 7.30–7.13 (m, 4H), 3.16 (s, 2H), 2.59 (s, 3H), m/z (ES$^+$) 358 (M+H)$^+$.

b) 3-(5-Methyl-3-phenylisoxazol-4-yl)-2,4-dihydroindeno[1,2-c]pyrazole-6-carboxylic acid methylamide 5-Methyl-3-phenylisoxazole-4-carboxylic acid (57 mg, 0.2 mmol) was stirred with 1,1'-carbonyldiimidazole (33 mg, 0.2 mmol) in tetrahydrofuran (2 ml) for 1 h, methylamine (1 ml of 33% solution in ethanol) was added and stirred for 1 h. The solvent was evaporated, the residue dissolved in EtOAc and washed with 1N HCl (×2), $H_2O$, ammonium hydroxide solution (×2) and $H_2O$ and dried ($MgSO_4$) and evaporated. The residue was purified on a silica prep plate eluting with 50% EtOAc/dichloromethane to give the title compound (5 mg, 7%). 1H NMR (360 MHz, $CDCl_3$) δ 7.86 (s, 1H), 7.78 (d, J=8.0 Hz, 1H), 7.72 (d, J=7.7 Hz, 1H), 7.51 (d, J=8.2 Hz, 2H), 7.44–7.36 (m, 3H), 6.15 (brs, 1H), 3.30 (s, 2H), 3.03 (d, J=4.8 Hz, 3H), 2.59 (s, 3H), m/z ($ES^+$) 371 $(M+H)^+$.

EXAMPLE 11

3-(5-Methyl-3-phenylisoxazol-4-yl)-2,4-dihydroindeno[1,2-c]pyrazole-6-carboxylic acid dimethylamide Prepared in the same way as Example 10 using dimethylamine (0.5 ml of a 2M solution in THF) to give the title compound (8 mg, 10%). $^1$H NMR (360 MHz, $CDCl_3$) δ 7.74 (d, J=7.8 Hz, 1H), 7.51 (d, J=8.3 Hz, 2H), 7.44–7.34 (m, 5H), 3.16 (s, 2H), 3.12 (brs, 3H), 3.02 (brs, 3H), 2.60 (s, 3H) m/z ($ES^+$) 385 $(M+H)^+$.

EXAMPLE 12

3-(5-Methyl-3-phenylisoxazol-4-yl)-2,4-dihydroindeno[1,2-c]pyrazole-6-carboxylic acid ethylamide Prepared in the same way as Example 10 using ethylamine (1 ml of a 33% solution in methylated spirits) to give the title compound (17 mg, 22%). $^1$H NMR (360 MHz, $CDCl_3$) δ 7.84 (s, 1H), 7.72 (s, 2H), 7.49 (d, J=8.1 Hz, 2H), 7.43–7.33 (m, 3H), 6.16 (brs, 1H), 3.55–3.47 (m, 2H), 3.26 (s, 2H), 2.57 (s, 3H), 1.26 (t, J=7.3 Hz, 3H), m/z ($ES^+$) 385 $(M+H)^+$.

EXAMPLE 13

6-(1-methyl-1H-imidazol-2-yl)-3-(5-methyl-3-phenylisoxazol-4-yl)-2,4-dihydroindeno[1,2-c]pyrazole To a suspension of 6-bromo-(5-methyl-3-phenylisoxazol-4-yl)-1,4-dihydroindeno[1,2-c]pyrazole (0.2 g, 0.51 mmol) and 1-methyl-2-tributylstannyl-1H-imidazole (0.75 g, 2 mmol) in DMF (8 ml) under an inert atmosphere was added tetrakis (triphenylphosphine)palladium (0) (0.1 g, 50% w/w). The reaction was heated to 100° C. for 16 h. Solvent was removed in vacuo and azeotroped with xylene and the residue was dissolved in dichloromethane and washed with water (2×). The organic layer was dried ($Na_2SO_4$), filtered and evaporated to yield a residue which was purified by column chromatography on silica using isohexane and ethyl acetate (1:1) to yield title compound (4 mg, 2%), $^1$H NMR (400 MHz, $CDCl_3$) δ 7.80 (d, J=7.6 Hz, 1H), 7.6 (1H, s), 7.58–7.51 (3H, m), 7.42–7.35 (3H, m), 7.10 (1H, s), 6.91 (1H, s), 3.76 (3H, s), 3.41 (2H, s), 2.58 (3H, s), m/z ($ES^{30}$) 394 $(M+H)^+$.

EXAMPLE 14

3-(5-Methyl-3-phenylisoxazol-4-yl)-6-pyridin-3-yl-2,4-dihydroindeno[1,2c]pyrazole Prepared in the same way as example 13, using 3-(1,1,1-tributylstannyl)pyridine. $^1$H NMR (360 MHz, $CDCl_3$) δ 8.90 (1H, s) 8.60 (d, J=4.4 Hz, 1H), 7.90 (dd, J=3.8 Hz and 1.6 Hz, 1H), 7.85 (d, J=7.9 Hz, 1H), 7.64 (1H, s), 7.60 (d, J=7.8 Hz, 1H), 7.55–7.52 (2H, m), 7.44–7.36 (4H, m), 3.37 (2H, s), 2.60 (3H, s), m/z ($ES^+$) 391 $(M+H)^+$.

EXAMPLE 15

3-(5-Methyl-3-phenylisoxazol-4-yl)-6-pyridin-4-yl-2,4-dihydroindeno[1,2c]pyrazole Prepared in the same way as Example 13, using 4-(1,1,1-tributylstannyl)pyridine. m/z ($ES^+$) 391 $(M+H)^+$.

EXAMPLE 16

3-[3-(4-Fluorophenyl)-5-methylisoxazol-4-yl]-2,4-dihydroindeno[1,2-c]pyrazole

Prepared in the same way as Example 1 using the acid chloride derived from 3-(4-fluorophenyl)-5-methylisoxazole-4-carboxylic acid (WO-A-0129015) to obtain the title compound as a white solid $^1$H NMR (360 MHz, $CDCl_3$) δ 7.73 (d, J=7.4 Hz, 1H), 7.54–7.51 (2H, m), 7.41 (d, J=7.4 Hz, 1H), 7.38 (t, J=7.4 Hz, 1H), 7.29 (t, J=7.4 Hz, 1H), 7.08–7.03 (2H, m), 3.30 (2H, s), 2.56 (3H, s), m/z ($ES^+$) 332 $(M+H)^+$.

EXAMPLE 17

3-[3-(2-Fluorophenyl)-5-methylisoxazol-4-yl]-2,4-dihydroindeno[1,2-c]pyrazole

Prepared in the same way as Example 1 using the acid chloride derived from 3-(2-fluorophenyl)-5-methylisoxazole-4-carboxylic acid (WO 2000-EP 10144) to obtain the title compound as a white solid $^1$H NMR (360 MHz, $CDCl_3$) δ 7.71 (d, J=7.4 Hz, 1H), 7.53–7.20 (6H, m), 7.11 (dt, J=1 and 8.4 Hz, 1H), 3.22 (2H, s), 2.64 (3H, s), m/z ($ES^+$) 332 $(M+H)^+$.

EXAMPLE 18

3-[3-(4-Fluorophenyl)-5-methylisoxazol-4-yl]-6,7-dimethoxy-2,4-dihydroindeno[1,2-c]pyrazole Prepared in the same way as Example 6 using 5,6-dimethoxyindanone and 3-(4-fluorophenyl)-5-methylisoxazole-4-carboxylic acid (WO 2000-EP 10144) to obtain the title compound as a white solid $^1$H NMR (360 MHz, $CDCl_3$) δ 7.54–7.50 (2H, m), 7.31 (1H, s), 7.08–7.03 (2H, m), 6.99 (1H,s), 3.94 (3H, s), 3.92 (3H,s), 3.25 (2H, s), 2.55 (3H, s), m/z ($ES^+$) 392 $(M+H)^+$.

EXAMPLE 19

3-(5-Methyl-3-(4-pyridyl)isoxazol-4-yl)-2,4-dihydroindeno[1,2-c]pyrazole a) Methyl (5-methyl-3-(4-pyridyl)isoxazol-4-yl) carboxylate Sodium (0.400 g, 0.0166 mol) was added to anhydrous methanol under nitrogen. After complete dissolution, the reaction vessel was cooled to 0° C. and methyl acetoacetate (1.8 ml, 0.166 mol) added. A solution of N-hydroxy-4-pyridine carboximidoyl chloride (2 g, 0.0128 mol; prepared according to Kocevar, M., Synth. Commun., 1988, 18(12), 1427) was added dropwise over 20 minutes. The reaction was stirred at 25° C. for 16 h, and quenched with acetic acid (1 ml). The methanol was removed in vacuo and the product partitioned between EtOAc and water. The organic layer was collected, dried over $MgSO_4$, and evaporated. The residue was chromatographed on silica eluting with 20% EtOAc/hexane→EtOAc to obtain the title compound as a beige solid (1.2 g). $^1$H NMR (400 MHz, $CDCl_3$) δ 8.73–8.71 (m, 2H), 7.57–7.56 (m, 2H), 3.80 (s, 3H), 2.77(s, 3H).

b) (5-Methyl-3-(4-pyridyl)isoxazol-4-yl)-N,O-dimethyl amide

The compound from part a) together with N,O-dimethyl hydroxylamine hydrochloride (0.67 g, 0.0069 mol) were dissolved in THF (10 ml) and cooled to −20° C. Isopropyl magnesium chloride (2.0M solution in THF, 7 ml, 0.0138 mol) was added dropwise over 5 minutes and the reaction stirred for a further 0.5 h. After quenching the reaction mixture with ammonium chloride (saturated), the product was extracted into EtOAc (3×). The organic layers were dried over $MgSO_4$ and evaporated. The residue was chromatographed on silica eluting with EtOAc to give the title compound as a white solid (0.77 g). m/z ($ES^+$) 248 $(M+H)^+$.

c) (5-Methyl-3-(4-pyridyl)isoxazol-4-yl)carboxaldehyde

The compound from part b) was dissolved in THF and cooled to 0° C. under nitrogen. Lithium aluminium hydride (1.0M in THF, 3.4 ml, 0.0034 mol) was added dropwise and the reaction stirred at 0° C. for 20 minutes. Hydrochloric acid (0.5 ml) was added till the hydride reagent was quenched, and $MgSO_4$ was added until a granular precipitate was formed. The reaction mixture was diluted with EtOAc and filtered through Hyflo™. The solvent was evaporated and the residue chromatographed on silica eluting with EtOAc to give the title compound as a white solid (0.58 g). m/z ($ES^+$) 189$(M+H)^+$.

d) 3-(5-Methyl-3-(4-pyridyl)isoxazol-4-yl)-2,4-dihydroindeno[1,2-c]pyrazole

Prepared in the same way as Example 3 using the compound from part c) and 1-indanone. $^1$H NMR (360 MHz, $CDCl_3$) δ 8.62–8.60 (m, 2H), 7.72 (d, J=7.45 Hz, 1H), 7.47–7.28 (m, 6H), 3.32 (s, 2H), 2.57 (s, 3H). m/z ($ES^+$) 315 $(M+H)^+$.

EXAMPLE 20

1-(5-Methyl-3-phenylisoxazol-4-yl)-2,8-dihydro-2,3,4-triazacyclopenta[a]indene a) 3-Bromopyridine-2-carboxylic acid methyl ester Sodium hydride (0.238 g of a 60% dispersion in mineral oil, 5.95 mmol) was added to a stirred solution of 3-bromopyridine-2-carboxylic acid (1.00 g, 4.95 mmol) in DMF (18mL) at 0° C. under nitrogen. The mixture was stirred for 50 min and methyl iodide (0.31 mL, 4.98 mmol) was then added dropwise. The mixture was allowed to warm up gradually to room temperature and was stirred for 2 days. Water was added and the mixture evaporated in vacuo. The residue was partitioned between dichloromethane and water and the aqueous layer separated and re-extracted with dichloromethane (×2). The combined organic layers were dried ($MgSO_4$) and evaporated in vacuo and the residue purified by flash chromatography on silica gel, eluting with 80% ethyl acetate in hexane, to give the title-ester (0.77 g, 72%), 1H NMR (400 MHz, $CDCl_3$) δ 8.62 (1H, dd, J=4.6 and 1.4 Hz), 8.01 (1H, dd, J=8.2 and 1.4 Hz), 7.31 (1H, dd, J=8.2 and 4.6 Hz), 4.02 (3H, s).

b) 1-(5-Methyl-3-phenylisoxazol-4-yl)propenone

A solution of tributyl(vinyl)tin (2.74 mL, 9.47 mmol) in chloroform (8 mL) was added dropwise to a solution of 5-methyl-3-phenylisoxazole 4-carbonyl chloride (2.00 g, 9.02 mmol) and trans-benzyl(chloro)bis(triphenylphosphine)palladium (II) (36 mg, 0.048 mmol) in chloroform (2 mL) at room temperature under dry air. The solution was stirred at 68° C. for 1.5 h at which time a second portion of benzyl(chloro)bis(triphenylphosphine)palladium (II) (9 mg) was added and the mixture stirred at 68° C. for a further 1.5 h. The mixture was diluted with diethyl ether and washed with water. The ethereal layer was separated, shaken with aqueous potassium fluoride solution and mixture aged for 0.25 h, at which time the resulting white precipitate (tributyltin fluoride) was filtered off through a pad of celite. This process was repeated (×1). The resulting ethereal filtrate was washed with brine (×1), dried ($MgSO_4$) and evaporated in vacuo. The residue was partitioned between acetonitrile and isohexane and the acetonitrile layer separated, washed with isohexane (×2) and evaporated in vacuo. The residue was purified by flash chromatography on silica gel, eluting with 15% ethyl acetate in isohexane, to give the title-compound (1.453 g, 76%), 1H NMR (360 MHz, $CDCl_3$) δ 7.54–7.44 (5H, m), 6.37–6.24 (2H, m), 5.66 (1H, dd, J=9.4 and 2.5 Hz), 2.68 (3H, s).

c) 3-[3-(5-Methyl-3-phenylisoxazol-4-yl)-3-oxo-propenyl]pyridine-2-carboxylic acid methyl ester A mixture of 1-(5-methyl-3-phenylisoxazol-4-yl)propenone (223 mg, 1.05 mmol), palladium acetate (15 mg, 0.067 mmol) and tri(o-tolyl)phosphine (40 mg, 0.13 mmol) in acetonitrile (3 mL) was degassed at room temperature. Triethylamine (0.26 mL, 1.9 mmol), 3-bromopyridine-2-carboxylic acid methyl ester (202 mg, 0.935 mmol) and copper (I) iodide (12 mg, 0.063 mmol) were added sequentially and the mixture degassed again. The reaction mixture was heated at reflux overnight, cooled to room temperature and partitioned between ethyl acetate and water. The organic layer was separated, dried ($MgSO_4$) and evaporated in vacuo. The residue was purified by flash chromatography on silica gel, eluting with 60–80% ethyl acetate in hexane (gradient elution), to give the title-compound (99 mg, 30%) as a mixture of olefin isomers, m/z ($ES^+$) 348 $(M+H)^+$.

d) 1-(5-Methyl-3-phenylisoxazol-4-yl)-2,8-dihydro-2,3,4-triaza-cyclopenta[a]indene A solution of the preceding enone (41 mg, 0.12 mmol) and 10% palladium on carbon (4 mg, 10% w/w) in a mixture of 70% perchloric acid (0.015 mL, 0.17 mmol) and ethanol (3 mL) was stirred under a hydrogen atmosphere for 2.5 h. The solvents were evaporated it vacuo and the residue partitioned between dichloromethane and water. The mixture was basified with solid potassium carbonate and the organic layer separated. The aqueous layer was re-extracted with dichloromethane (×1) and the combined organic layers dried ($MgSO_4$) and evaporated in vacuo to afford crude 3-[3-(5-methyl-3-phenylisoxazol-4-yl)-3-oxo-propyl]pyridine-2-carboxylic acid methyl ester (39 mg), m/z ($ES^+$) 351 $(M+H)^+$.

Sodium hydride (7 mg of a 60% dispersion in mineral oil, 0.18 mmol) was added to a stirred solution of 3-[3-(5-methyl-3-phenylisoxazol-4-yl)-3-oxopropyl]pyridine-2-carboxylic acid methyl ester (39 mg, 0.11 mmol) in THF at 0°

C. under nitrogen. The mixture was stirred at 0° C. for 70 min and at room temperature for 15 min. Water was added and the mixture diluted with dichloromethane and the aqueous layer neutralised with aqueous ammonium chloride solution. The aqueous layer was separated and re-extracted with dichloromethane (×1) and the combined organic layers dried (MgSO$_4$) and evaporated it vacuo to give crude 6-(5-methyl-3-phenylisoxazole-4-carbonyl)-5,6-dihydro-[1]-pyridin-7-one (34 mg), m/z (ES$^+$) 319 (M+H)$^+$.

A mixture of 6-(5-methyl-3-phenylisoxazole-4-carbonyl)-5,6-dihydro-[1]-pyridin-7-one (32 mg, 0.10 mmol), hydrazine hydrochloride (28 mg, 0.41 mmol) and sodium acetate trihydrate (55 mg, 0.40 mmol) in 1:1 ethanol/water (2 mL) was heated at reflux under nitrogen for 21 h. Aqueous work-up followed by purification by flash chromatography on silica gel gave the title-compound, 1H NMR (360 MHz, CDCl$_3$) δ 8.57 (1H, br d, J=4.7 Hz), 7.67–7.15 (7H, m), 2.91 (2H, s), 2.66 (3H, m); m/z (ES$^+$) 315 (M+H)$^+$.

The invention claimed is:
1. A compound of formula (I):

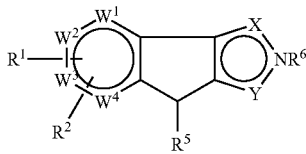

in which:
one of X and Y is a nitrogen atom substituted by a group R$^{6'}$ and the other is a carbon atom substituted by an isoxazole group substituted on its carbon atoms by groups R$^3$ and R$^4$;
either all of W$^1$, W$^2$, W$^3$ and W$^4$ are carbon or one of W$^1$, W$^2$, W$^3$ and W$^4$ is nitrogen and the rest are carbon;
R$^1$ and R$^2$ are each, independently,
(i) hydrogen, halogen, cyano, amino, nitro, hydroxy, aminocarbonyl, C$_{1-6}$alkyl, C$_{2-6}$alkenyl, C$_{2-6}$alkynyl, C$_{1-6}$alkoxy, C$_{2-6}$alkenyloxy, C$_2$alkynyloxy, hydroxy C$_{1-6}$alkyl, C$_{1-6}$alkoxyC$_{1-6}$alkyl, aminoC$_{1-6}$alkyl, C$_{1-6}$alkylcarbonyl, C$_{1-6}$alkylaminocarbonyl or di(C$_{1-6}$alkyl)aminocarbonyl, each of which is unsubstituted or substituted by one, two or three halogen atoms;
(ii) a 5-membered heteroaromatic ring containing 1,2, 3 or 4 heteroatoms independently selected from O, N or S, at most one of the heteroatoms being oxygen or sulphur, or a 6-membered aromatic ring optionally containing one or two nitrogen atoms, said rings being unsubstituted or substituted by at least one substituent which is halogen, hydroxy, cyano, amino, C$_{1-6}$alkyl, C$_{2-6}$alkenyl, C$_{2-6}$alkynyl, C$_{1-6}$alkoxy, C$_{2-6}$alkenyloxy, C$_2$alkynyloxy, C$_{1-6}$alkoxyC$_{1-6}$alkyl, hydroxyC$_{1-6}$alkyl, aminoC$_{1-6}$alkyl, C$_{1-6}$alkylcarbonyl or C$_{1-6}$alkylaminocarbonyl, each of which substituents is itself, where possible, unsubstituted or substituted by one, two or three halogen atoms;
(iii) a cyclic amine ring having from 4 to 7 members, one of which is nitrogen which is the point of attachment of said ring to the rest of the molecule and optionally containing 1 additional heteroatom selected from O and N, said ring being unsubstituted or substituted by at least one substituent which is halogen, hydroxy, cyano, amino, C$_{1-6}$alkyl, C$_{2-6}$alkenyl, C$_{2-6}$alkynyl, C$_{1-6}$alkoxy, C$_{2-6}$alkenyloxy, C$_2$alkynyloxy, C$_{1-6}$alkoxyC$_{1-6}$alkyl, aminoC$_{1-6}$alkyl, C$_{1-6}$alkylcarbonyl or C$_{1-6}$alkylaminocarbonyl, each of which substituent is itself, where possible, unsubstituted or substituted by one, two or three halogen atoms;
R$^3$ and R$^4$ are independently hydrogen, halogen, hydroxy, aminocarbonyl, C$_{1-6}$alkyl, C$_{2-6}$alkenyl, C$_{2-6}$alkynyl, C$_{1-6}$alkoxy, C$_{2-6}$alkenyloxy, C$_{2-6}$alkynyloxy, C$_{1-6}$alkoxyC$_{1-6}$alkyl, aminoC$_{1-6}$alkyl, C$_{1-6}$alkylthio, hydroxyC$_{1-6}$alkyl, C$_{1-6}$alkylaminoC$_{1-6}$alkyl, C$_{1-6}$alkylcarbonyl or C$_{1-6}$alkylaminocarbonyl, each of which is unsubstituted or substituted by one, two or three halogen atoms; or a 5-membered heteroaromatic ring containing 1, 2, 3 or 4 heteroatoms independently selected from O, N and S, at most one of the heteroatoms being oxygen or sulphur, or a 6-membered aromatic ring optionally containing 1 or 2 nitrogen atoms, the rings being unsubstituted or substituted by at least one halogen, hydroxy, aminocarbonyl, C$_{1-6}$alkyl, C$_{2-6}$alkenyl, C$_{2-6}$alkynyl, C$_{1-6}$alkoxy, C$_{2-6}$alkenyloxy, C$_{2-6}$alkynyloxy, hydroxyC$_{1-6}$alkyl, C$_{1-6}$alkoxyC$_{1-6}$alkyl, aminoC$_{1-6}$alkyl, C$_{1-6}$alkylcarbonyl or C$_{1-6}$alkylaminocarbonyl, each of which is unsubstituted or substituted by one, two or three halogen atoms;
R$^5$ is hydrogen, halogen, hydroxy, aminocarbonyl, C$_{1-6}$alkyl, C$_{2-6}$alkenyl, C$_{2-6}$alkynyl, C$_{1-6}$alkoxy, C$_{2-6}$alkenyloxy, C$_2$alkynyloxy, C$_{1-6}$alkoxyC$_{1-6}$alkyl, aminoC$_{1-6}$alkyl, C$_{1-6}$alkylcarbonyl or C$_{1-6}$alkylaminocarbonyl; and
one of R$^6$ and R$^{6'}$ is hydrogen and the other is absent;
or a pharmaceutically acceptable salt thereof.

2. The compound of claim 1 in which W$^1$ is nitrogen or carbon and W$^2$, W$^3$ and W$^4$ are carbon.

3. The compound of claim 1 in which R$^1$ is hydrogen, halogen, cyano, C$_{1-4}$alkyl, C$_{1-4}$alkoxy, C$_{1-4}$alkylaminocarbonyl, di(C14alkyl)aminocarbonyl, aminocarbonyl, a 5- or 6-membered heterocyclic ring containing 1 or 2 nitrogen heteroatoms or 1 sulphur heteroatom and optionally substituted by a C$_{1-6}$alkyl group.

4. The compound of claim 1 in which R$^2$ is hydrogen or C$_{1-4}$alkoxy.

5. The compound of claim 1 in which:
R$^1$ and R$^2$ each, independently, represents hydrogen, fluoro, chloro, bromo, cyano, C$_{1-6}$alkyl, C$_{1-6}$alkoxy, aminocarbonyl, C$_{1-6}$alkylaminocarbonyl, di(C$_{1-6}$)alkylaminocarbonyl, N,N-diethylaminocarbonyl, pyridyl or methylimidazolyl;
R$^3$ represents a methyl group;
R$^4$ represents phenyl, fluorophenyl or pyridyl;
R$^5$ represents hydrogen; and
one of R$^6$ and R$^{6'}$ represents hydrogen and the other is absent;
or a pharmaceutically acceptable salt thereof.

6. A compound which is selected from the group consisting of:
3-(5-methyl-3-phenylisoxazol-4-yl)-2,4-dihydroindeno[1,2-c]pyrazole;
3-(5-methyl-3-phenylisoxazol-4-yl)-2,8-dihydroindeno[2,1-c]pyrazole;
6-methoxy-3-(5-methyl-3-phenylisoxazol-4-yl)-2,4-dihydroindeno[1,2-c]pyrazole;
7-methoxy-3-(5-methyl-3-phenylisoxazol-4-yl)-2,4-dihydroindeno[1,2-c]pyrazole;
5-methoxy-3-(5-methyl-3-phenylisoxazol4-yl)-2,4-dihydroindeno[1,2-c]pyrazole;
6,7-dimethoxy-3-(5-methyl-3-phenylisoxazol-4-yl)-2,4-dihydroindeno[1,2-c]pyrazole;
3-(5-methyl-3-phenylisoxazol-4-yl)-2,4-dihydroindeno[1,2-c]pyrazole-6-carbonitrile;

3-(5-methyl-3-phenylisoxazol-4-yl)-2,4-dihydroindeno[1,2-c]pyrazole-6-carboxylic acid amide;
3-(5-methyl-3-phenylisoxazol-4-yl)-5-(2-methyl-2H-pyrazol-3-yl)-2,4-dihydroindeno[1,2-c]pyrazole;
3-(5-methyl-3-phenylisoxazol-4-yl)-2,4-dihydroindeno[1,2-c]pyrazole-6-carboxylic acid methylamide;
3-(5-methyl-3-phenylisoxazol-4-yl)-2,4-dihydroindeno[1,2-c]pyrazole-6-carboxylic acid dimethylamide;
3-(5-methyl-3-phenylisoxazol-4-yl)-2,4-dihydroindeno[1,2-c]pyrazole-6-carboxylic acid ethylamide;
6-(1-methyl-1H-imidazol-2-yl)-3-(5-methyl-3-phenylisoxazol-4-yl)-2,4-dihydroindeno[1,2-c]pyrazole;
3-(5-methyl-3-phenylisoxazol-4-yl)-6-pyridin-3-yl-2,4-dihydroindeno[1,2-c]pyrazole;
3-(5-methyl-3-phenylisoxazol-4-yl)-6-pyridin-4-yl-2,4-dihydroindeno[1,2-c]pyrazole;
3-[3-(4-fluorophenyl)-5-methylisoxazol-4-yl]-2,4-dihydroindeno[1,2-c]pyrazole;
3-[3-(2-fluorophenyl)-5-methylisoxazol-4-yl]-2,4-dihydroindeno[1,2-c]pyrazole;
3-[3-(4-fluorophenyl)-5-methylisoxazol-4-yl]-6,7-dimethoxy-2,4-dihydroindeno[1,2-c]pyrazole;
3-(5-methyl-3-(4-pyridyl)isoxazol-4-yl)-2,4-dihydroindeno[1,2-c]pyrazole; and
1-(5-methyl-3-phenylisoxazol-4-yl)-2,8-dihydro-2,3,4-triazacyclopenta[a]indene;
or a pharmaceutically acceptable salt thereof.

7. A pharmaceutical composition comprising a compound of claim 1 or a pharmaceutically acceptable salt thereof and a pharmaceutically acceptable excipient.

8. A method of treating a subject suffering from Alzheimer's Disease, which comprises administering to that subject a therapeutically effective amount of a compound of claim 1 or a pharmaceutically acceptable salt thereof.

* * * * *